United States Patent [19]
Bonutti

[11] Patent Number: 5,343,580
[45] Date of Patent: Sep. 6, 1994

[54] INDEXING ASSEMBLY FOR SHOULDER IMAGING

[75] Inventor: Peter M. Bonutti, Effingham, Ill.

[73] Assignee: Apogee Medical Products, Inc., Effingham, Ill.

[21] Appl. No.: 950,600

[22] Filed: Sep. 24, 1992

Related U.S. Application Data

[63] Continuation-in-part of Ser. No. 802,358, Dec. 4, 1991.

[51] Int. Cl.$^5$ .......................... A61B 6/04; A47C 20/00
[52] U.S. Cl. ........................................... 5/601; 5/623; 5/647; 378/208; 74/813 C
[58] Field of Search ................... 5/601, 623, 646, 647, 5/628, 648, 650; 378/208, 209; 74/817, 813 R, 813 C, 813 L; 128/653.1, 653.2, 653.5

[56] References Cited

U.S. PATENT DOCUMENTS

| | | | |
|---|---|---|---|
| 1,239,146 | 9/1917 | Wantz | 5/601 |
| 2,801,142 | 7/1957 | Adams | 5/623 |
| 2,972,505 | 2/1961 | Weickgenannt | 5/623 |
| 3,025,397 | 3/1962 | Travis | 378/208 |
| 3,124,328 | 3/1964 | Kortsch | 5/646 |
| 3,521,876 | 7/1970 | Smith | 5/601 |
| 3,528,413 | 9/1970 | Aydt | 5/647 |
| 4,050,355 | 9/1977 | Niskanen | 74/817 |
| 4,232,681 | 11/1980 | Tulaszewski . | |
| 4,256,112 | 3/1981 | Kopf | 378/208 |
| 4,291,229 | 9/1981 | Patt . | |
| 4,323,080 | 4/1982 | Melhart | 6/650 |
| 4,616,814 | 10/1986 | Harwood | 5/601 |
| 4,827,496 | 5/1989 | Cheney | 5/601 |

OTHER PUBLICATIONS

Attachment A: Topics in Magnetic Resonance Imaging/vol. 3, Issue 4.

Primary Examiner—Flemming Saether
Attorney, Agent, or Firm—Tarolli, Sundheim & Covell

[57] ABSTRACT

A self-contained shoulder indexing apparatus is for use during imaging of a shoulder joint of a patient, with the patient lying on an imaging table slidable into and out of a primary imaging coil. The self-contained shoulder indexing apparatus includes an index mechanism having an index member lockable in any selected one of a plurality of sequential index positions. Table attachment means connects the index mechanism with the table for sliding movement with the table. A cuff support member is connected with the index member for movement with the index member. A cuff supported on the cuff support member at a location remote from the index member for clamping onto the patient's arm. The cuff is connected with the support member for movement with the support member and with the index member and is lockable with the index member in any selected one of the plurality of sequential spaced index positions.

15 Claims, 11 Drawing Sheets

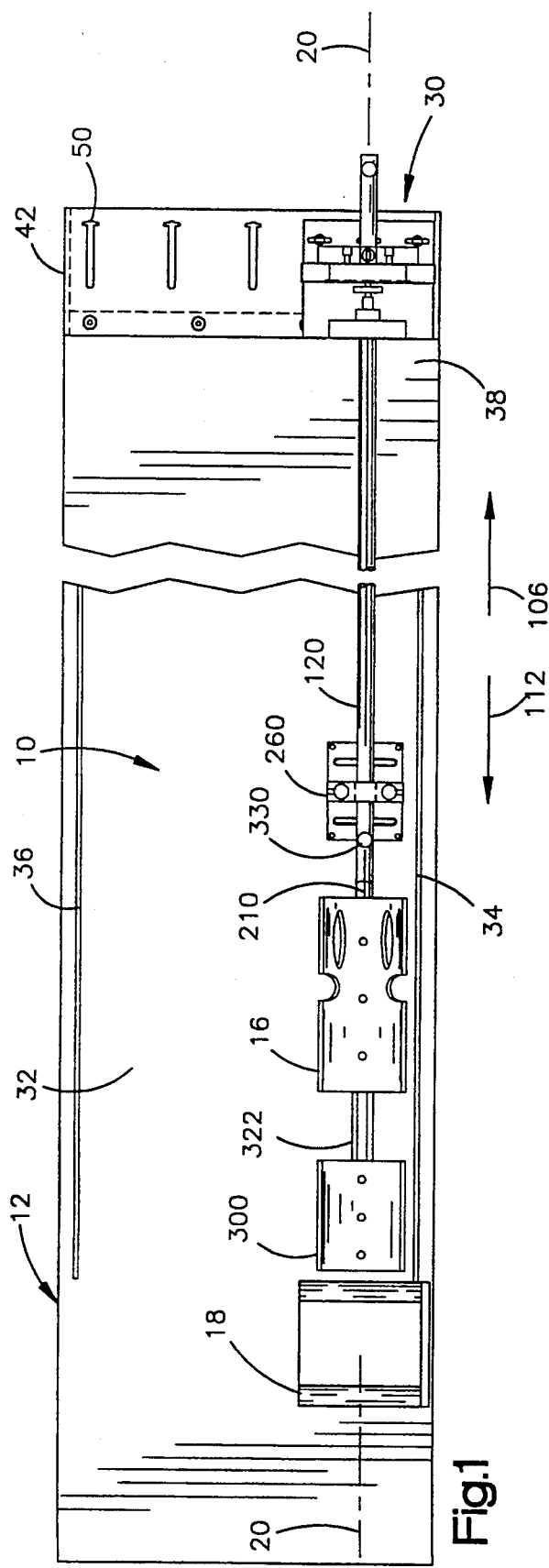
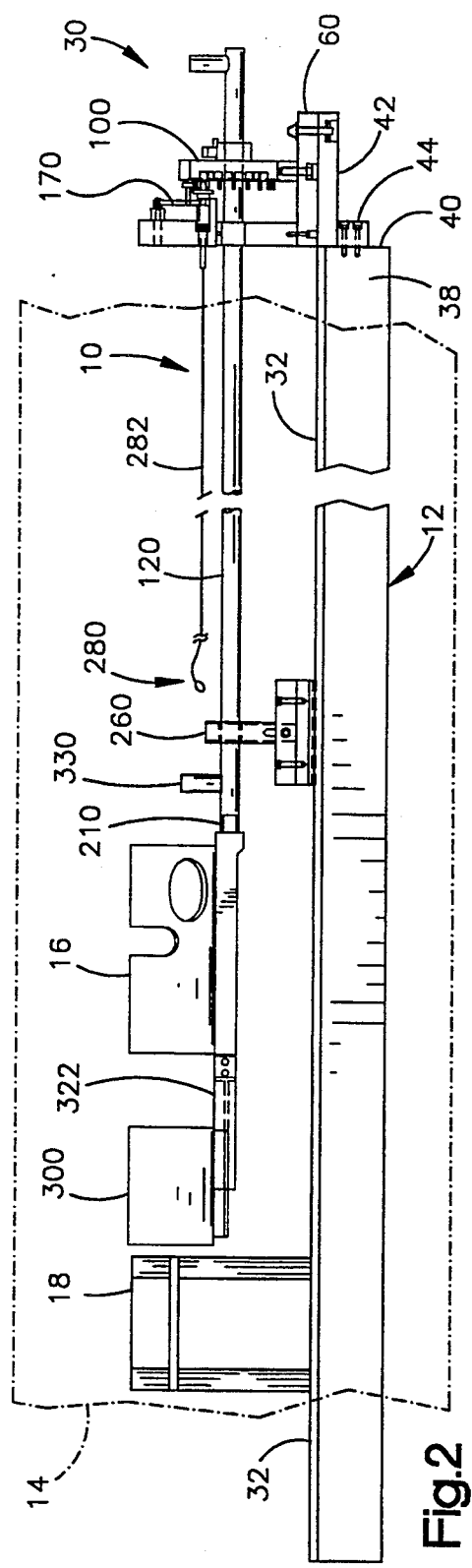
Fig.1
Fig.2

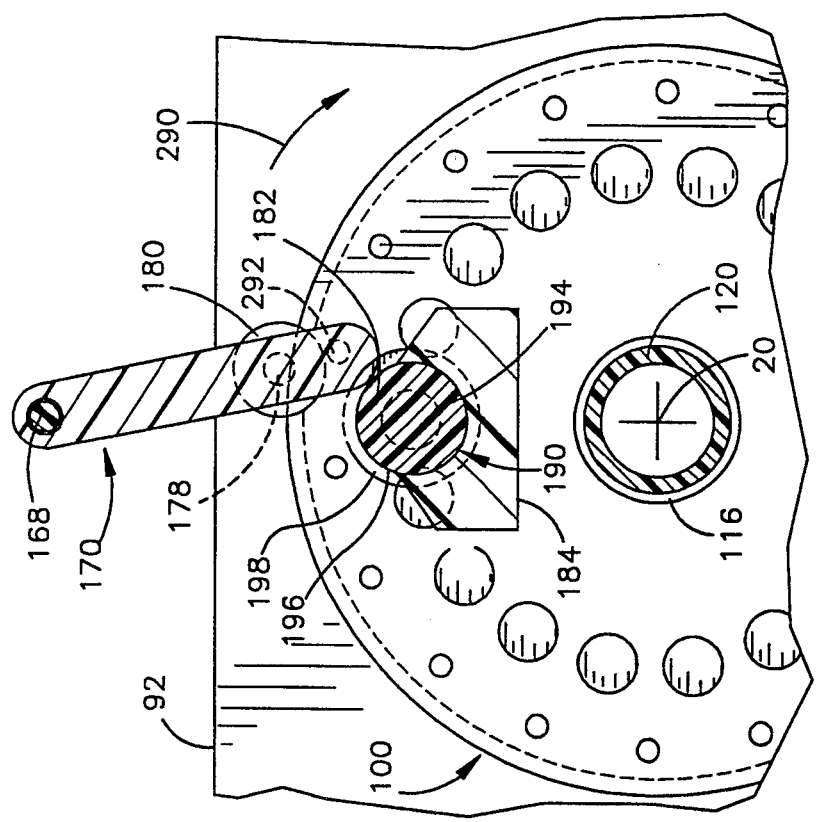
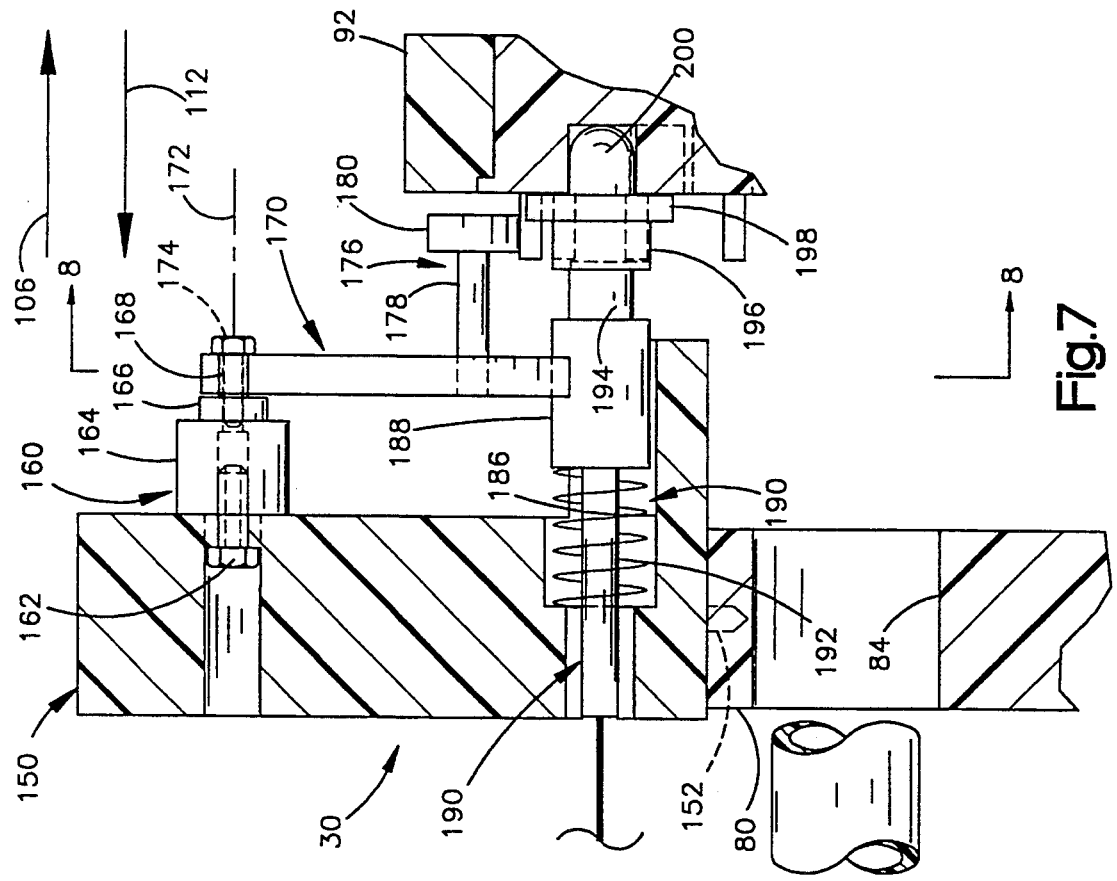
Fig.8
Fig.7

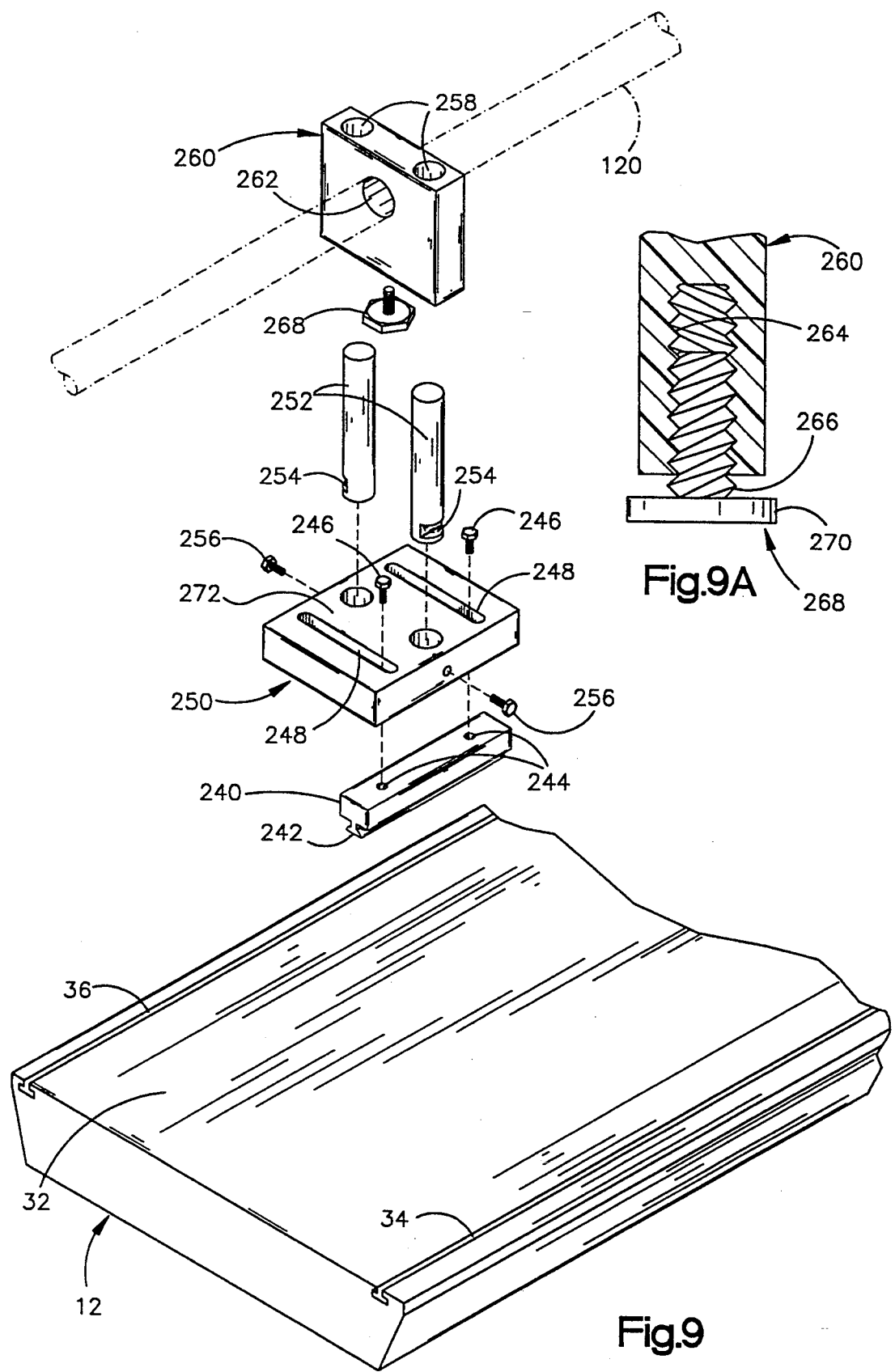

INDEXING ASSEMBLY FOR SHOULDER IMAGING

RELATED APPLICATION

This application is a continuation-in-part of patent application Ser. No. 07/802,358, filed Dec. 4, 1991, naming Peter M. Bonutti as inventor, the benefit of the filing date of which is hereby claimed.

BACKGROUND OF THE INVENTION

The present invention relates to an indexing assembly for use in imaging of a joint in the human body. In the preferred embodiment, the present invention is an indexing assembly for use in moving a shoulder joint through its range of motion during imaging of the shoulder joint in a magnetic resonance imaging ("MRI") apparatus.

Static imaging of a joint, that is imaging of the joint in only one orientation, may not disclose joint abnormalities or defects which are visible in kinematic imaging of the joint. Kinematic imaging of the joint takes a series of images of the joint at different orientations of the joint.

It would be desirable to have an indexing assembly for use in imaging in a primary MRI coil which provides the capability of accurate and repeatable kinematic indexing a joint such as a shoulder joint. The indexing assembly should preferably be patient directed.

SUMMARY OF THE INVENTION

A self-contained shoulder indexing apparatus is for use during imaging of a shoulder joint of a patient, with the patient lying on an imaging table slidable into and out of a primary imaging coil. The self-contained shoulder indexing apparatus includes an index mechanism having an index member lockable in any selected one of a plurality of sequential index positions. Table attachment means connects the index mechanism with the table for sliding movement with the table. A cuff support member is connected with the index member for movement with the index member. A cuff supported on the cuff support member at a location remote from the index member for clamping onto the patient's arm. The cuff is connected with the support member for movement with the support member and with the index member and is lockable with the index member in any selected one of the plurality of sequential spaced index positions.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein:

FIG. 1 is a top plan view of an indexing assembly in accordance with the present invention, connected with a table for use inside a primary imaging coil of a magnetic resonance imaging apparatus;

FIG. 2 is a side elevational view of the indexing assembly and table of FIG. 1;

FIG. 7 is an enlarged view similar to FIG. 5A showing the index assembly in a locked condition;

FIG. 8 is an enlarged view taken along line 8—8 of FIG. 7 showing the index assembly in a locked condition;

FIG. 9 is an exploded perspective view of a free guide assembly which is part of the index assembly of FIG. 1;

FIG. 9A is an enlarged view of a portion of the free guide assembly of FIG. 9;

DESCRIPTION OF A PREFERRED EMBODIMENT

Figure 3:
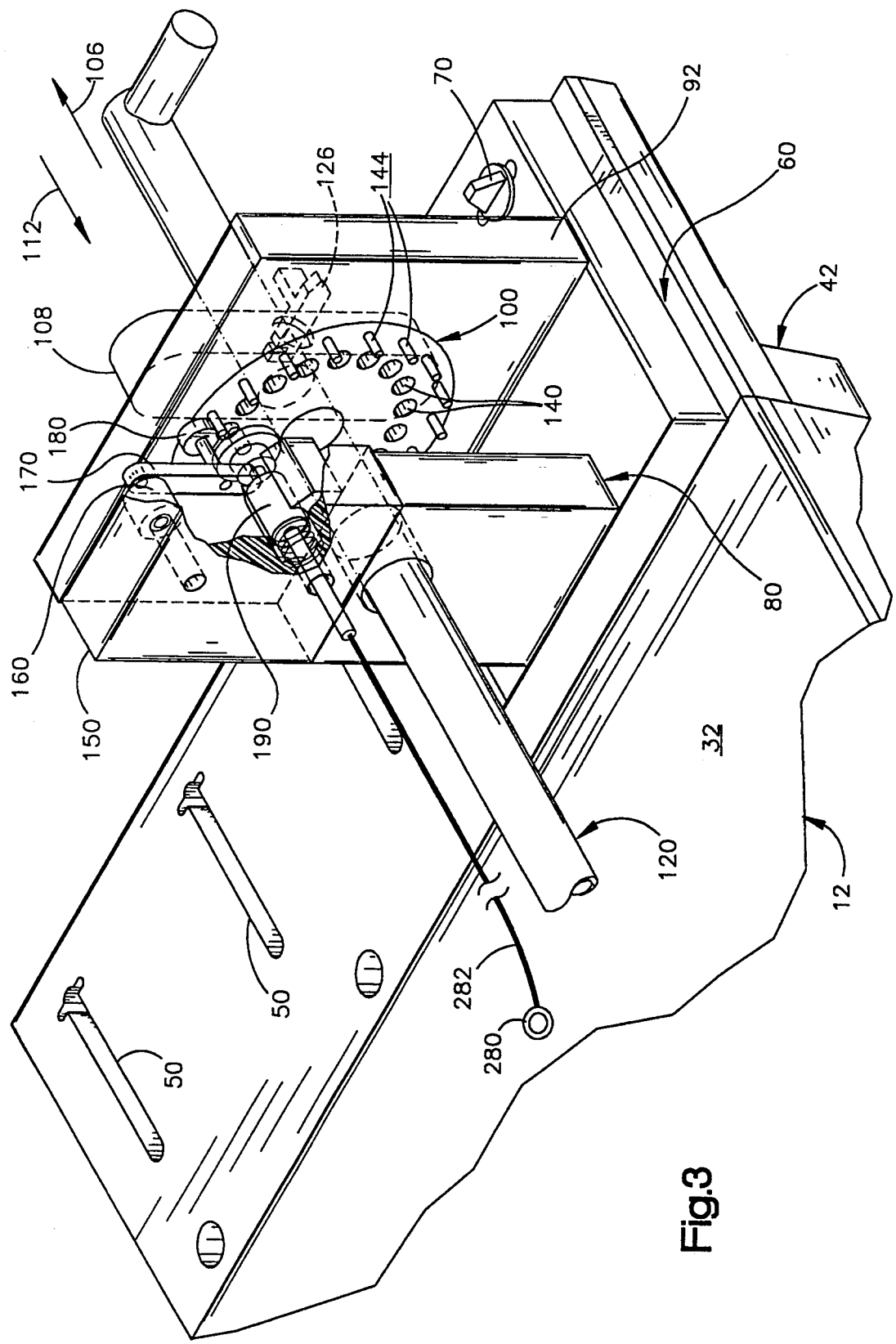
FIG. 3 is a perspective view of a portion of the indexing assembly of FIG. 1.
Figure 4:
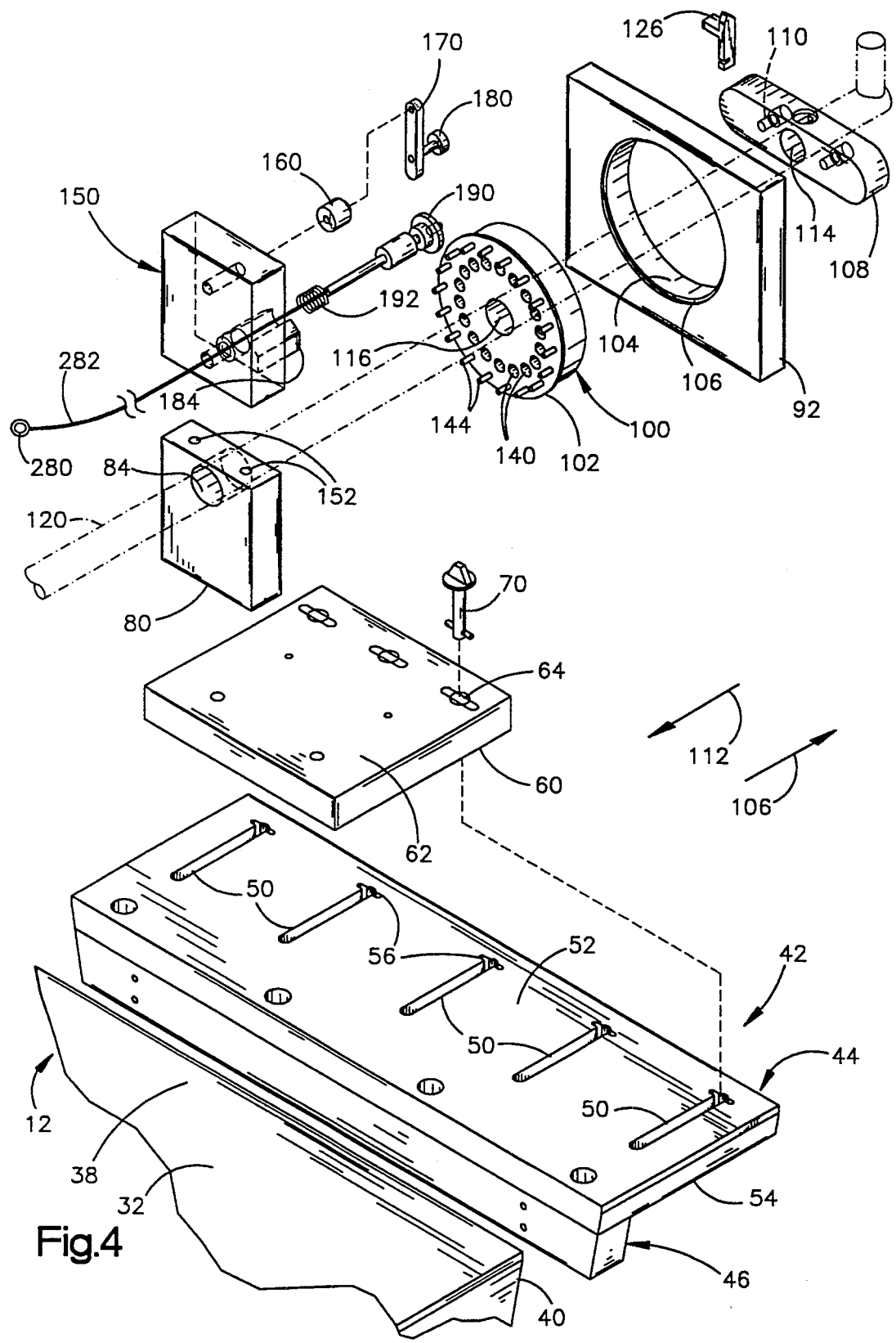
FIG. 4 is an exploded perspective view of the index assembly of FIG. 3.

The present invention relates generally to an index assembly for use in imaging of a joint of a patient. As representative of the present invention, FIG. 1 illustrates an index assembly 10 for use in imaging the shoulder of a joint of a patient (not shown). The index assembly 10 is described in detail below, as is its operation. In brief, the patient lies on a known imaging table 12 which is slidable into and out of a known primary imaging coil 14 shown schematically in FIG. 2. The patient lies on his back, with his head to the left and his feet to the right (as viewed in FIGS. 1 and 2). The patient's right hand is secured in a cuff 16, with the palm facing up. The patient's shoulder is disposed inside a known shoulder coil 18. To provide sequential imaging of the shoulder joint, a patient rotates his hand and arm about an axis 20. The rotation of the hand and arm, and the placement of the shoulder joint in the sequential index positions spaced apart a known number of degrees, and facilitated by an index mechanism 30 which is part of the overall indexing assembly 10.

The imaging table 12 is generally flat, having an upper major side surface 32 on which the patient lies. The imaging table 12 has two grooves 34 and 36 in its upper major side surface 32. The grooves 34 and 36 extend longitudinally along the table 12 for the length of the table, near the outer longitudinal edges of the table. The table 12 has an end portion 38 near or supporting the patient's feet, to the right as viewed in FIGS. 1 and 2.

The table end portion 38 has an end surface 40 to which is attached a table extension 42. The table extension 42 is made of two parts, an upper portion 44 and a lower portion 46, held together by suitable fasteners (not shown). Four screws 48 extend through the table extension lower portion into the table end portion 38, to secure the table extension 42 to the table 12. The table extension 42 may alternatively be made of one part only, if feasible.

The table extension 42 has five longitudinally extending slots 50. The slots 50 extend downward through the upper portion 44 of the table extension 42, from its upper major side surface 52 to its lower major side surface 54. Each slot 50 has a keyhole opening 56 at its outer end.

An indexer base 60 is disposed on the upper major side surface 52 of the table extension 42. The indexer base 60 has an upper major side surface 62. Three keyhole openings 64 extend vertically through the indexer base 60.

A hold-down 70 extends through a selected one of the keyhole openings 64 in the indexer base 60, and into one of the slots 50 in the table extension 42. A cross-pin 72 at the lower end of the hold-down 70 is received in a widened slot portion 74 in the table extension 42. When the hold-down 70 is rotated 90°, the hold-down secures the indexer base 60 to the table extension 42.

A fixed guide 80 is located on the upper major side surface 62 of the indexer base 60 at its inner end (to the left as viewed in FIGS. 1–4). Two screws 82 extend up through the indexer base 60 into the fixed guide 80, to secure the fixed guide 80 to the indexer base 60. The fixed guide 80 has a central passage 84.

An indexer body 92 is also disposed on the upper major side surface 62 of the indexer base 60. Two screws 94 extend up through the indexer base 60 into the indexer body 92 to secure the indexer body to the indexer base.

An index disk 100 is rotatably received in the indexer body 92. The index disk 100 has a radially outwardly extending lip 102 engaged against a shoulder 104 on the indexer body 92. The engagement of the index disk lip 102 with the shoulder 104 blocks axial movement of the indexer disk 100 relative to the indexer body 92, in a direction from the patient's head toward the patient's foot—i.e., to the right as viewed in FIGS. 1–5 as indicated by the arrow 106. The index disk 100 is circular in shape and is rotatable about the axis 20, within the indexer body 92.

A clamp block 108 is fixed to the index disk 100 for rotation with the index disk. Two screws (not shown) extend through counterbored openings 110 in the clamp block 108 and into the index disk 100, to secure the clamp block to the index disk. The length of the clamp block 108 is greater than the diameter of the index disk 100. The clamp block 108 thus blocks axial movement of the index disk 100 relative to the indexer body 92, in a direction from the patient's foot toward the patient's head—i.e., to the left as viewed in FIGS. 1–5, as indicated by the arrow 112. A central passage 114 in the clamp block 108, and a central passage 116 in the index disk 100, are coaxial with the central passage 84 in the fixed guide 80.

A support tube 120 extends through the coaxial aligned openings 114, 116, and 84. The support tube 120 is hollow and has a longitudinally extending central passage 122. A series of locking slots 124 are formed in the support tube 120, extending through the wall of the support tube into the central opening 122.

Figure 12:
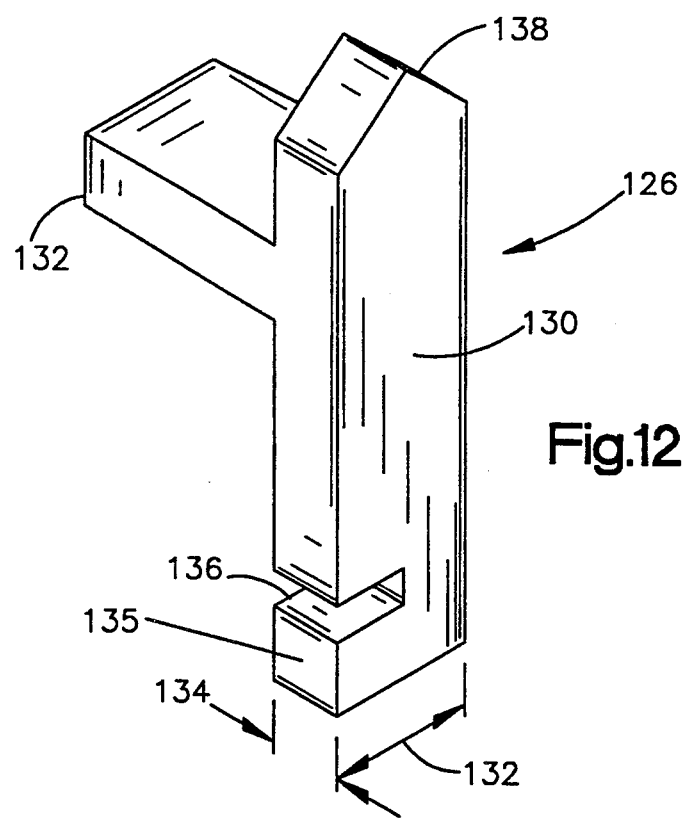
FIG. 12 is an enlarged view of a locked pointer portion of the index assembly of FIG. 1.
Figure 13:
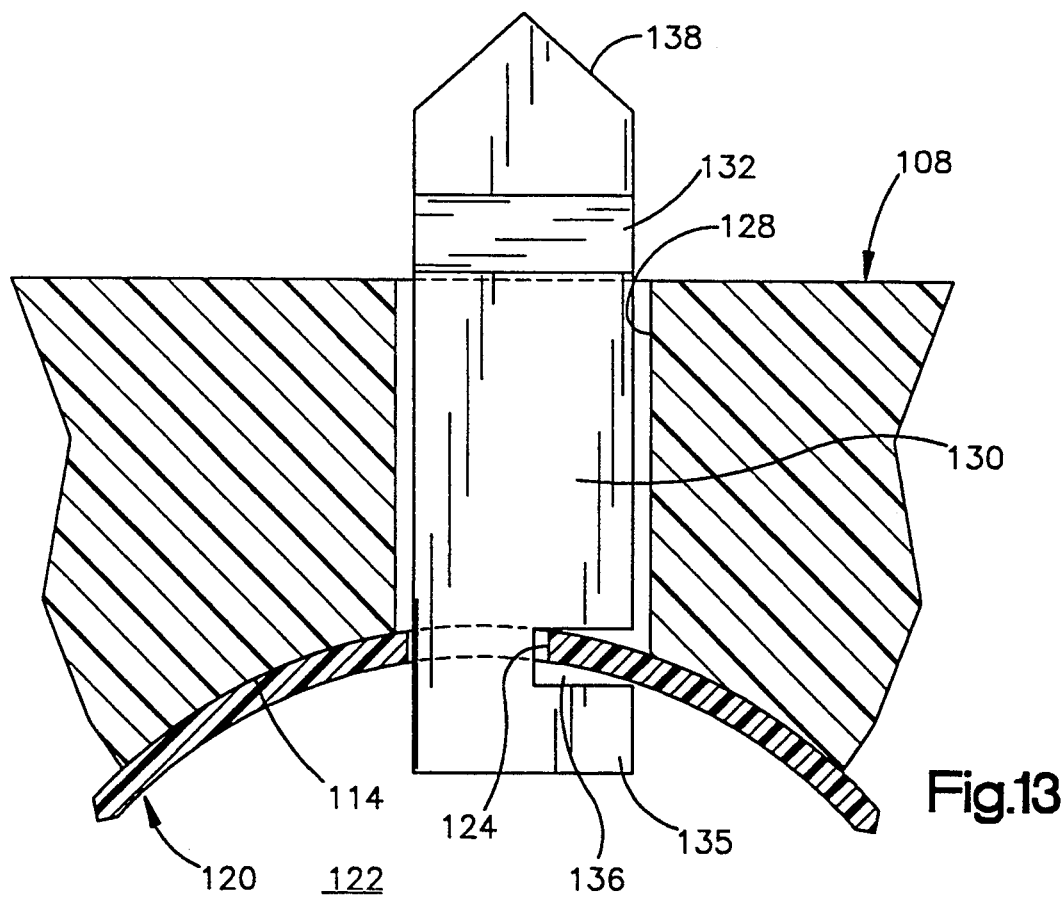
FIG. 13 is an enlarged view showing the locked pointer in engagement in the index assembly.

A lock pointer 126 (FIGS. 12 and 13) extends through an opening 128 in the clamp block 108, and through a selected one of the locking slots 124 in the support tube 120, and into the central passage 122 in the support tube. The lock pointer 126 has a main body portion 130 which is rectangular in cross-sectional configuration. The main body portion 130 has a longer dimension 132 and a shorter dimension 134. The longer dimension 132 of the lock pointer body portion 130 is slightly shorter than the diameter of the opening 128 of the clamp block 108. The lock pointer 126 has a handle portion 132. The lock pointer 126 also has a lower end portion 135 separated from the main body portion by a notch 136. The lock pointer also has a pointed outer end portion 138.

The lock pointer 126 is inserted through the opening 128 in the clamp block 108, in a rotational position such that the narrow dimension 134 of the lock pointer 126 fits through one of the slots 124 in the support tube 120. The lower end portion 135 is moved radially to a location inside the tube 120. The lock pointer 126 is then rotated so that the notch 136 engages around the wall of the support tube 120, thus locking the clamp block 108 to the support tube 120.

The pointed outer end portion 138 of the lock pointer 126 serves as an indicator to tell an MRI technician the rotational position of the support tube 120 (and of the cuff 16 which is fixed to the support tube). In the preferred embodiment, when the cuff 16 is opened upwardly as shown in FIGS. 1 and 2, the pointed outer end portion 138 of the lock pointer 126 is pointing vertically, and the clamp block 108 extends horizontally.

The index disk 100 has a set of plunger openings 140 disposed in a circular array about the axis 20. The plunger openings 140 extend axially part way into the index disk 100 in a direction as indicated by the arrow 106. The index disk 100 also has a set of trip pins 144 disposed in a circular array about the axis 20. The trip pins 174 project axially out of the index disk 100, in a direction as indicated by the arrow 112.

A trigger base 150 (FIG. 5A) is disposed atop the fixed guide 80. Two screws extend down through counterbored screw holes (not shown) in the trigger base 150, into screw holes 152 in the fixed guide 80, to secure the trigger base 150 to the fixed guide 80.

The trigger base 150 supports an arbor 160. A screw 162 secures the arbor 160 to the trigger base 150. The arbor 160 has a main body portion 164, an intermediate portion 166, and an end portion 168.

A trigger 170 hangs down from the end portion 168 of the arbor 160 and is supported for swinging movement on the arbor 160 about an axis 172. A screw 174 holds the trigger 170 on the arbor 160. The trigger 170 has a lower end portion 182. A trigger extension 176 projects axially from the trigger 170. The trigger extension 176 includes a shank portion 178 and an outer end portion 180.

The trigger base 150 has a plunger support portion 184 with a cylindrical opening 186 which extends back into the main body of the trigger base 150. A main body portion 188 of a plunger 190 is received in the opening 186. A compression spring 192 biases the plunger 190 in a direction to the right as viewed in FIGS. 1–5, as indicated by the arrow 106.

Figure 5:
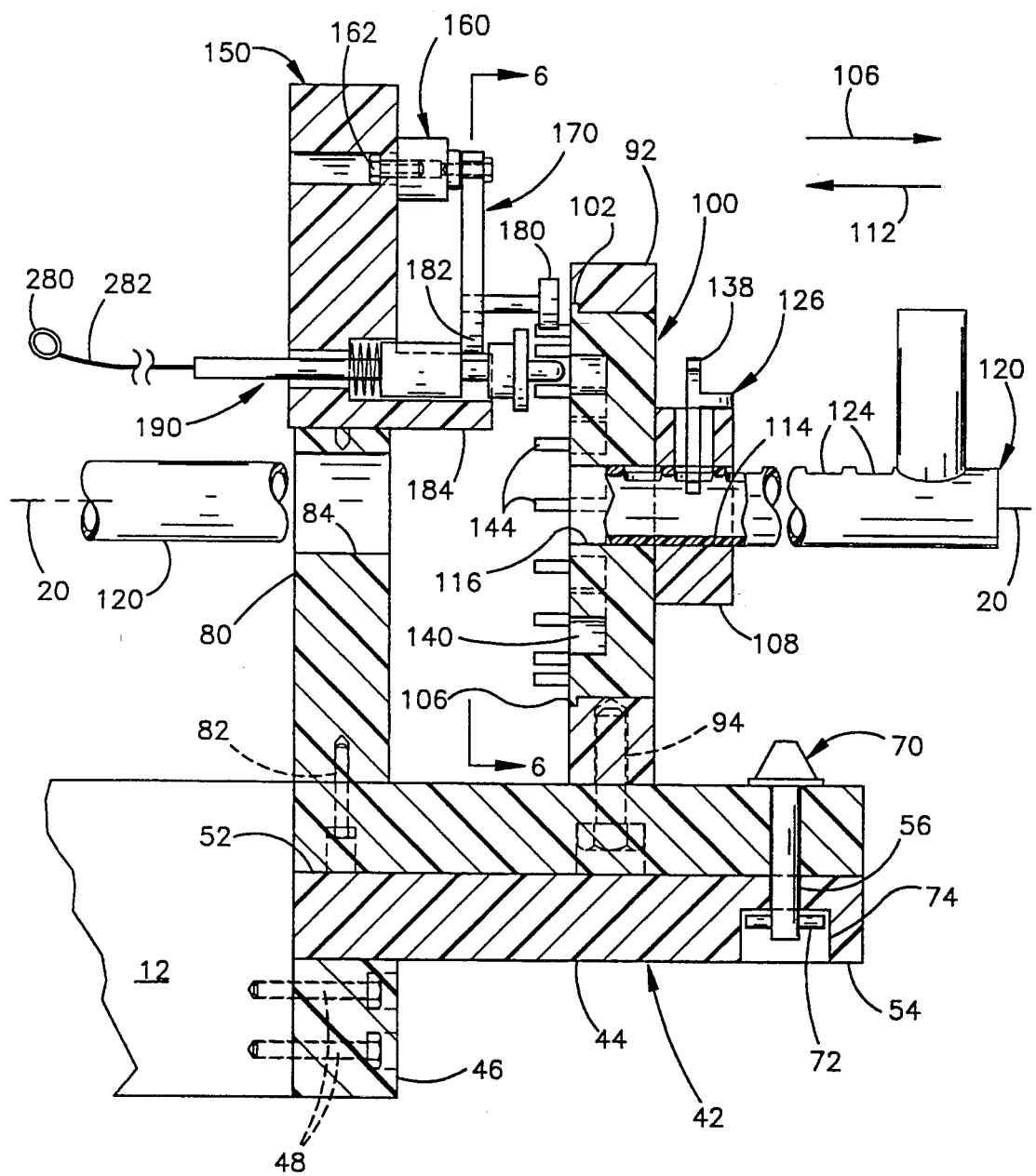
FIG. 5 is a longitudinal sectional view of the indexing assembly of FIG. 1.
Figure 5A:
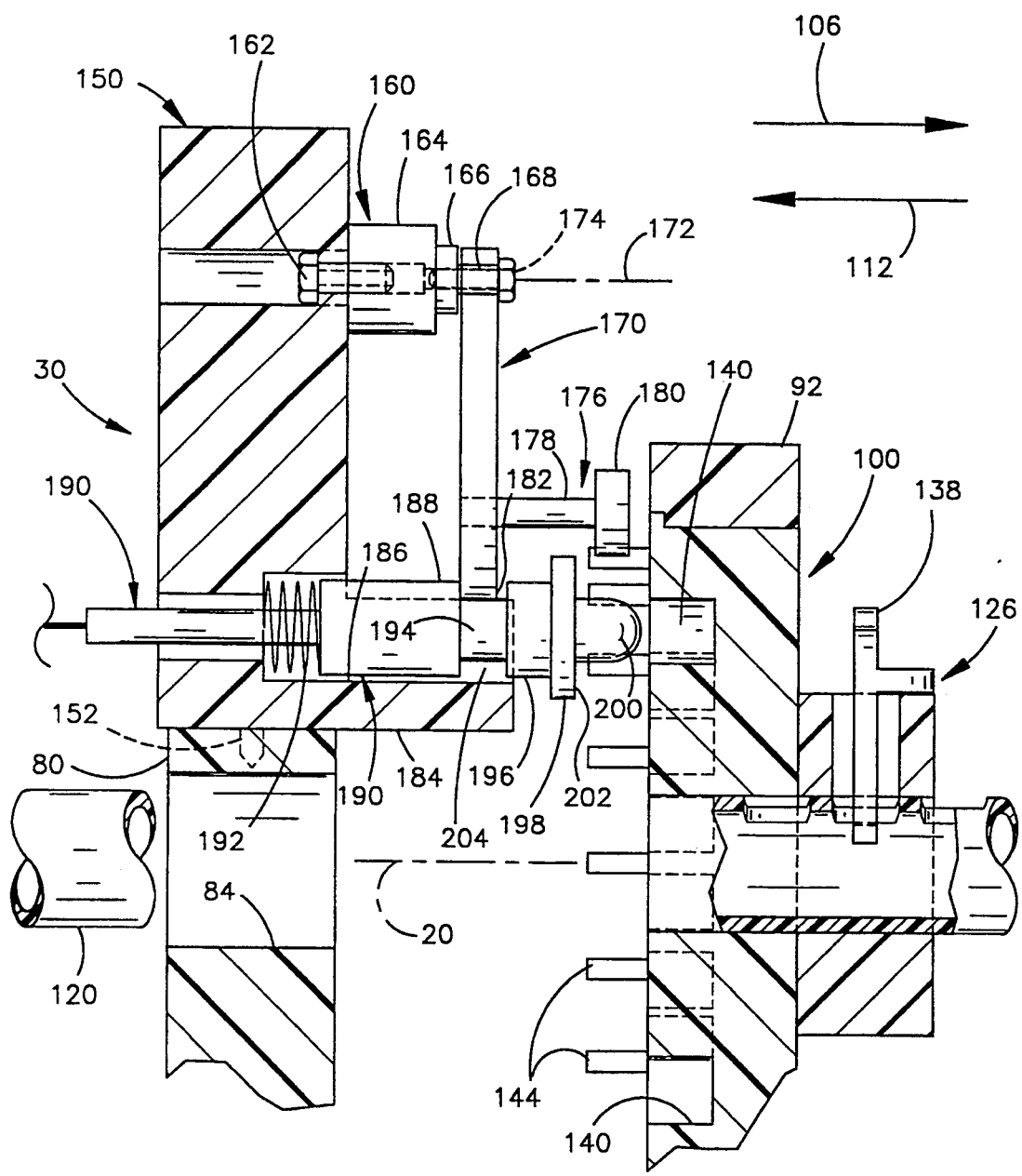
FIG. 5A is an enlarged view of a portion of FIG. 5.

The plunger 190 also has a reduced diameter shank portion 194, a second body portion 196, a third body portion 198, and a plunger tip portion 200. The third body portion 198 has a radially extending end face 202 facing toward the index disk 100. The plunger main body portion 186 and the plunger second body portion 196 define between them a longitudinally extending annular gap 204. When the plunger 190 is in the position as shown in FIG. 5A, i.e., retracted away from the index disk 100, the lower end portion 182 of the trigger 170 falls into the gap 204 in the plunger 190. The trigger 170 hangs straight down by its own weight.

Figure 10:
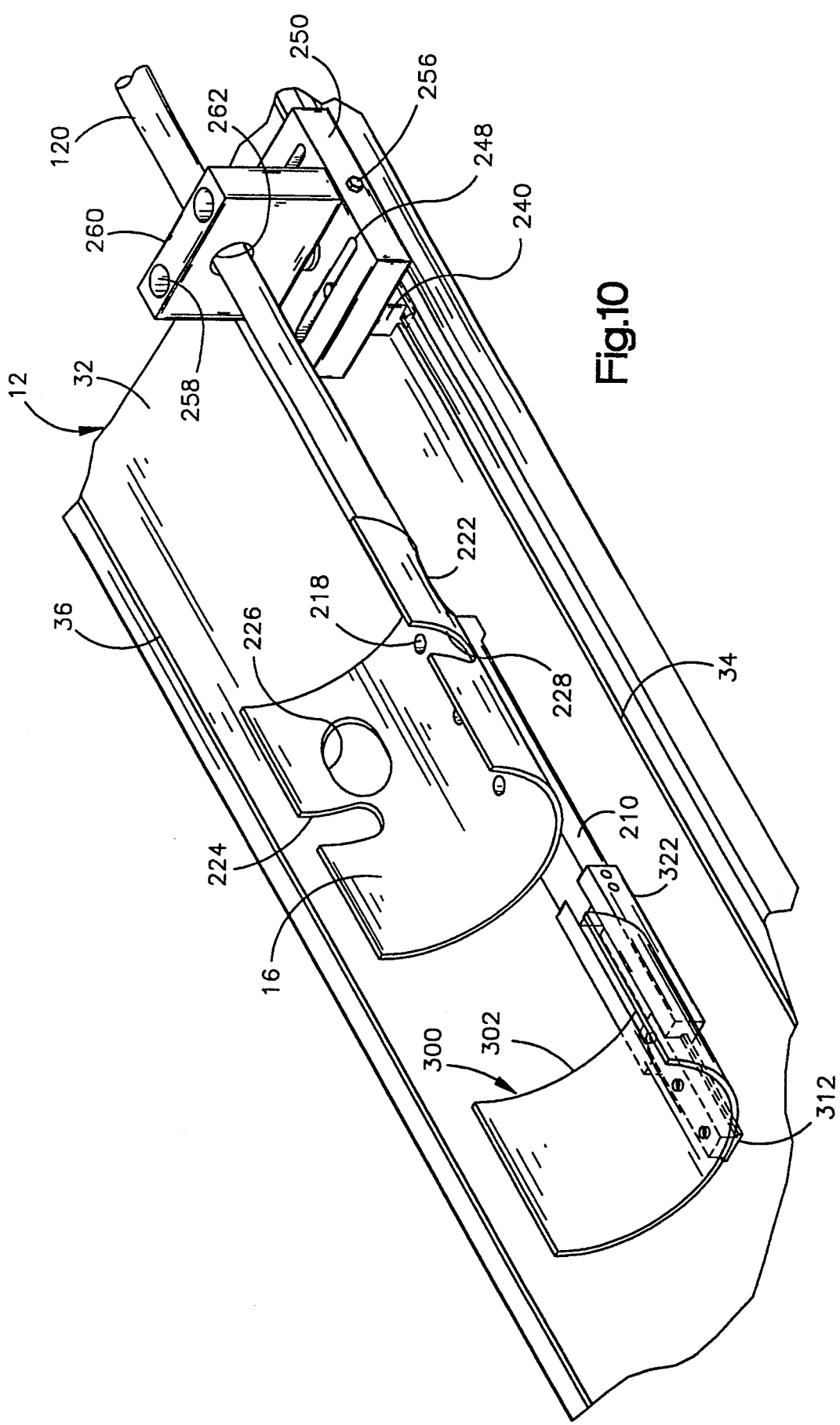
FIG. 10 is a perspective view of the cuff and free guide portions of the index assembly of FIG. 1.
Figure 11:
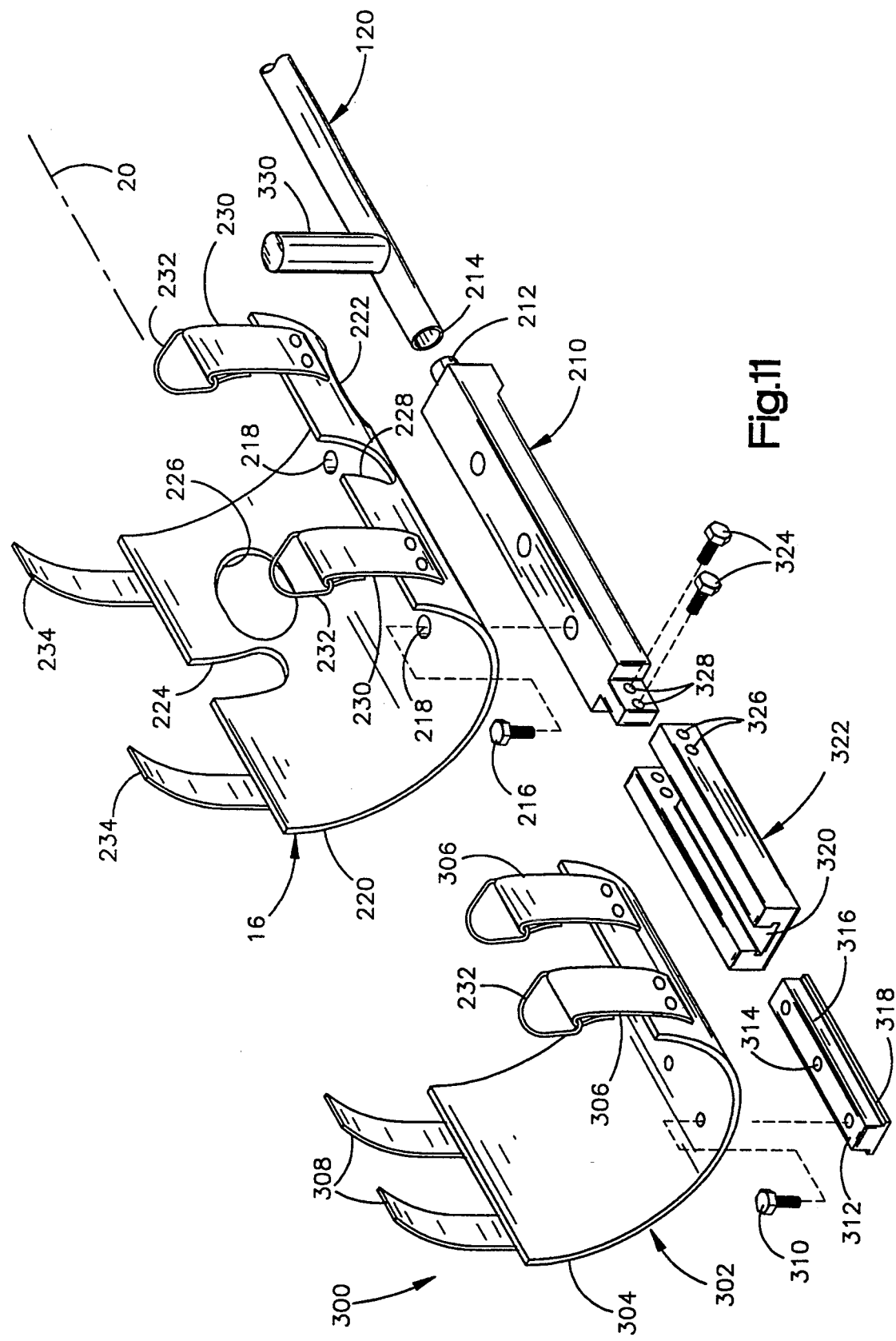
FIG. 11 is an exploded perspective view of the cuff portion.

Toward the other end of the index assembly 10, a paddle 210 (FIGS. 10 and 11) has a rounded end portion 212 which is press fit into an end portion 214 of the support tube 120. A plurality of screws 216 (only one of which is shown) extend through screw holes 218 in a plastic body portion 220 of the cuff 16. The screws 216 secure the cuff 16 to the paddle 210. The cuff 16 is bent into a semicylindrical shape about the axis 20. The cuff 16 has a thumb hole 222 for receiving the right thumb of the patient's hand, and a wrist bone opening 224 to allow room for the patient's wrist bone to extend out of the cuff 16. The cuff 16 also has a similar thumb hole 226 and wrist bone opening 228 for use when the patient's left hand is strapped in the cuff 16.

Two straps 230 extend from the one side of the plastic body portion 220 of the hand cuff 16. On the end of each strap 230 is a D-ring 232. A velcro strap 234 extending from the opposite side of the plastic body portion 220 of the cuff 16, is extensible through the D-ring 232 to secure the patient's hand to the cuff 16.

A free guide slider 240 (FIG. 9) has a longitudinally extending rib 242 which fits into one or the other of the grooves 34, 36 in the table 12. The slider 240 has two screw holes 244, spaced apart along the length of the slider, which receive respective screws 246 through respective slots 248 in a free guide base 250. The slots 240 are wider than the diameter of the shank portions of the screws 246. The slots 246 extend in a direction across the width of the table 12. Thus, when the screws 246 are inserted through the slots 248 into the slider 240, the free guide base 250 is movable across the width of the table 12 via the slots 248.

The free guide base 250 is also slidable along the length of the table 12 via the engagement of the rib 242 in the groove 34 or 36. Two free guide support posts 252 are connected with the free guide base 250 for movement with the free guide base. Each post 252 has a notch 254 near its lower end which receives a set screw 256. The posts 252 thus project upwardly from and are movable with the free guide base 250.

The posts 252 extend through post holes 258 in a free guide 260. The free guide 260 has a central passage 262 for receiving therethrough the support tube 120. Thus, the free guide 260 can move up and down on the posts 252, supporting the support tube 120 for vertical movement relative to the upper major side surface 32 of the table 12. The free guide 260 and the main tube 120 are thus movable in all directions relative to the table 12.

The free guide 120 has a threaded opening 264 which receives the threaded shank portion 266 of a thumb screw 268. The head portion 270 of the thumb screw 268 rides on the upper major side surface 272 of the free guide base 250. Rotation of the thumb screw 268 in the free guide 260 sets a lower limit of the vertical positioning of the free guide 260 on the free guide base 250.

In operation of the indexing assembly 10, the patient lies on his back on the imaging table 12, with his head to the left and his feet to the right as viewed in FIGS. 1 and 2. The patient's right hand is secured in the cuff 16, palm up. The patient's right thumb extends through the thumb hole 222. The wrist bone may extend outwardly of the plastic body 220 of the cuff 16 through the wrist bone opening 224. The patient's shoulder is inside the shoulder coil 18, which is a known secondary imaging coil. The table 12 is then slid axially inside the primary imaging coil 14.

The shoulder may first be imaged in the starting orientation. Then, the patient is instructed to move the shoulder joint to the next orientation. To do this, the patient first pulls on a finger grip 280 attached to an actuator cord 282. The actuator cord 282 is connected with the plunger 190. The actuator cord transmits the force of the patient's pulling action to the plunger 190, and the plunger is retracted from the engaged position shown in FIGS. 6 and 6A to the disengaged position shown in FIGS. 5 and 5A.

Figure 6A:
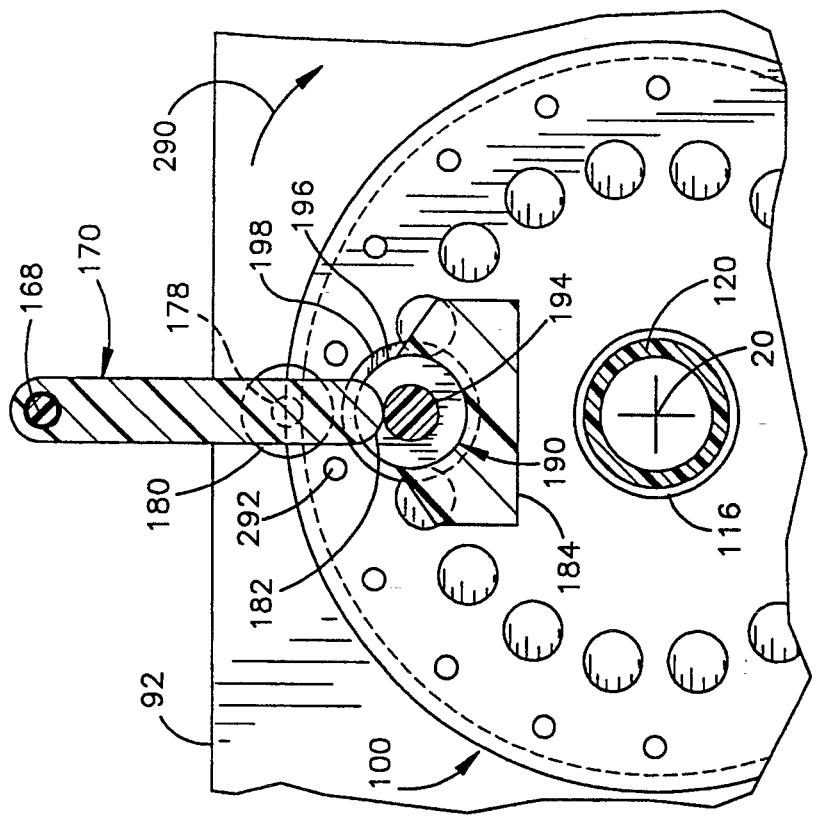
FIG. 6A is an enlarged view of a portion of FIG. 6.
Figure 6:
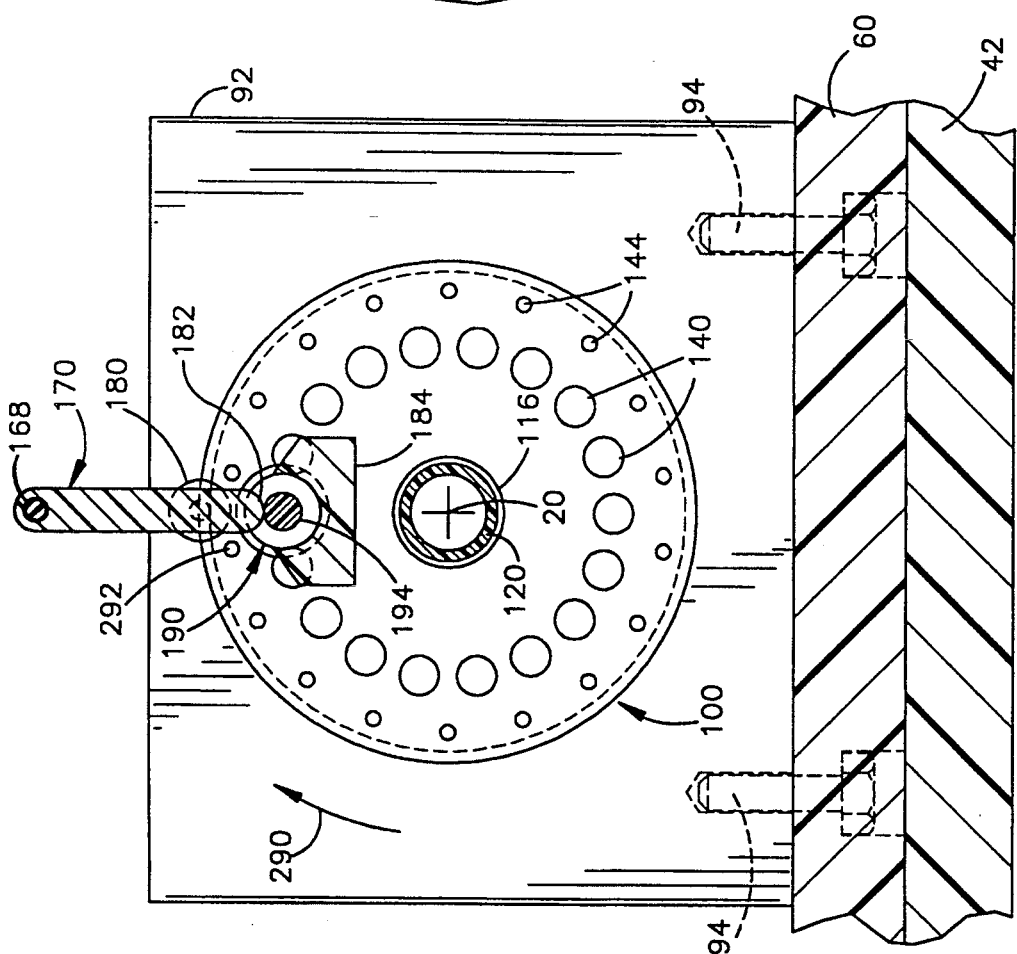
FIG. 6 is a transverse sectional view taken along line 6—6 of FIG. 5.

As the plunger is thus retracted, the gap 204 in the plunger moves axially into a position adjacent the lower end portion 182 of the trigger 170 (FIG. 5A). The trigger 170 is then free to pivot about the axis 172. The force of gravity causes the trigger 172 to assume a vertical position so that the lower end portion 182 of the trigger moves into the gap 204 in the plunger 190 (FIGS. 6, 6A). The trigger 170 then blocks axial movement of the plunger 190 toward the index disk 100. The plunger 190 is thus held away from the index disk 100, and the index disk is free to rotate about the axis 20.

Since the index disk 100 is connected through the main tube 120 with the cuff 16, the cuff 16 is now also free to rotate about the axis 20. The patient can then move his shoulder joint to the next orientation, as desired, by rotating his hand which is secured in the cuff 16. The patient may grasp a handle 330 secured to the main tube 120 to better assist in rotation of the cuff 16. As the patient rotates his hand, the cuff 16 and the index disk 100 rotate. If the patient is turning his hand inward, the index disk 100 rotates in a clockwise direction as viewed in FIG. 6, as indicated by the arrow 290.

As the index disk 100 rotates, the trip pins 144 and the plunger openings 140 revolve about the axis 20. One of the trip pins designated 292 in FIG. 6A, almost immediately engages the trigger extension 180, and pivots the trigger out of the gap 204 in the plunger 190. This allows the plunger 190 to move back toward the index disk 100 under the influence of the plunger spring 192. The plunger tip 200 engages the face of the index disk 100, then falls automatically into the next plunger opening 140 as the index disk 100 continues to rotate. The engagement of the plunger 190 in the plunger opening 140 limits movement of the plunger outwardly from the trigger base 150, in a direction to the right as indicated in FIG. 5A.

If more support is needed for the patient's arm, a biceps support assembly 300 (FIGS. 1-2, 10-11), can be provided. The biceps support assembly includes a biceps cuff 302 having a plastic body portion 304. Two straps 306 having D-rings thereon extend from one side of the biceps cuff 302. Two velcro straps 308 extend from the other side and can be looped through the D-rings and secured to themselves to clamp the patient's biceps firmly in the plastic body portion 304 of the biceps cuff 302.

A plurality of fasteners 310 (only one of which is shown) secure the plastic body portion 304 on the biceps cuff 302 to a biceps cuff slider 312. The fasteners 310 are received in fastener openings 314 on the upper surface of the biceps slider 312. The biceps slider 312 has a main body portion 316 and a lower lip portion 318. The lip portion 318 is received in a groove 320 in a paddle extension 322. The paddle extension 322 is secured with screws 324 through openings 326 in the paddle extension 322 and through openings 328 in the paddle 210.

The biceps cuff slider 312 is slidable in the groove 320 in the paddle extension 322. Since the paddle 322 is fixed relative to the paddle 210 and the main tube 120, the biceps cuff 302 is thus slidable in a direction parallel to the axis 20, relative to the hand cuff 16. Thus, the patient's biceps can be securely clamped in the biceps cuff assembly 300, to provide additional support and stability for the arm while it is being imaged, yet the biceps cuff assembly is slidable along the length of the table to provide for adjustment and movement during changing orientation.

The cuff 16 may be placed at different longitudinal positioned along the length of the table 12 relative to the index mechanism 30. The main tube 120 has a plurality of slots 124 adjacent the index mechanism 30. The lock pointer 126, as discussed above, is received in a selected one of these slots 124. To accommodate patients of different sizes, the lock pointer 126 may be disengaged from the position shown in FIG. 13, and moved radially outwardly of the main tube 120 so that the main tube 120 may be slid longitudinally along the axis 20 relative to the clamp block 108. When the cuff 16 is at the appropriate location to hold the patient's hand, the lock pointer 126 is inserted through the nearest slot 124 into the main tube 120, and secured therein, as described above.

As discussed above, the free guide 260 is relatively movable on the table 12. This movement accommodates shifting movement of the hand cuff 16 upon movement of the patient's hand or shoulder joint. For example, as the patient's hand is rotated inwardly, the arm tends to rise. The free guide 260 allows for this movement, sliding vertically upward along the free guide support posts 252.

The entire index mechanism 30 may be placed in different lateral positions on the table extension 42. As discussed above, three keyholes 64 are provided in the indexer base 60, while five slots 50 are provided in the table extension 42. The indexer base 60 may be secured to the table extension 42 with the hold-down 70 extending through any one of the three keyholes 64 into any one of the slots 52. Thus, a total of fifteen different positions are available for the indexer base 60, laterally across the width of the table extension 42. This can accommodate imaging of patients with different physical characteristics, as well as, of course, imaging of the right or the left hand. For imaging of the left hand, the free guide 260 would be placed in the groove 36 (FIG. 1) on the opposite side of the table 12.

From the above description of the invention, those skilled in the art will perceive improvements, changes and modifications in the invention. Such improvements, changes and modifications within the skill of the art are intended to be covered by the appended claims.

I claim:

1. Self-contained shoulder indexing apparatus for use during imaging of a shoulder joint of a patient, with the patient lying on an imaging table slidable into and out of a primary imaging coil, said self-contained shoulder indexing apparatus comprising:
   an index mechanism having an index member lockable in any selected one of a plurality of sequential index positions;
   table attachment means for connecting said index mechanism with the table for sliding movement with the table;
   a cuff support member connected with said index member for movement with said index member; and
   a cuff supported on said cuff support member at a location remote from said index member for clamping onto the patient's arm, said cuff being connected with said support member for movement with said support member and with said index member and being lockable with said index member in any selected one of the plurality of sequential spaced index positions;
   said index mechanism including limiting means for ensuring movement of said index member into the next one of said sequential index positions upon movement of said index member out of any one of said sequential index positions;
   wherein said limiting means includes an index locking member movable between an engaged position in locking engagement with said index member and a disengaged position not in locking engagement with said index member, and a trigger mechanism connected with said index mechanism and movable between a first condition blocking movement of said index locking member into the engaged position and a second condition freeing said index locking member for movement into the engaged position.

2. Self-contained shoulder indexing apparatus for use during imaging of a shoulder joint of a patient, with the patient lying on an imaging table slidable into and out of a primary imaging coil, said self-contained shoulder indexing apparatus comprising:
   an index mechanism having an index member lockable in any selected one of a plurality of sequential index positions;
   table attachment means for connecting said index mechanism with the table for sliding movement with the table;
   a cuff support member connected with said index member for movement with said index member; and
   a cuff supported on said cuff support member at a location remote from said index member for clamping onto the patient's arm, said cuff being connected with said support member for movement with said support member and with said index member and being lockable with said index member in any selected one of the plurality of sequential spaced index positions;
   said index mechanism including limiting means for ensuring movement of said index member into the next one of said sequential index positions upon movement of said index member out of any one of said sequential index positions;
   wherein said index member comprises an index disk rotatable with said cuff member, said index disk having surfaces defining a plurality of index openings disposed in a circular pattern on said index disk, said index openings revolving along a circular path as said index disk rotates; said index mechanism includes a plunger mounted for sliding movement toward and away from said index disk openings; said index mechanism includes a trigger mechanism connected with said index mechanism and having a first condition blocking movement of the plunger toward said index disk openings when the plunger is retracted away from said index disk by the patient and a second condition freeing the plunger for movement toward said index disk openings, said trigger mechanism being moved from the first condition to the second condition as a result of rotation of said index disk by force transmitted from the patient through said cuff member and said support member.

3. An apparatus as set forth in claim 2 wherein said trigger mechanism includes:

a plurality of trip pins disposed in a circular pattern on said index disk and revolving along a circular path as said index disk rotates; and a trigger extending into the path of revolution of said trip pins for engagement by at least one of said trip pins when said trip pins revolve with said index disk.

4. A shoulder indexing apparatus for use during imaging of a shoulder joint of a patient, with the patient lying on an imaging table slidable into and out of a primary imaging coil, said shoulder indexing apparatus comprising:

an index mechanism having an index member lockable in any selected one of a plurality of sequential index positions;

table attachment means connected with said index mechanism for attaching said index mechanism to the table;

a cuff support member connected with said index member for movement with said index member; and a cuff supported on said cuff support member for movement with said support member at a location remote from said index member for clamping onto the patient's arm, said index member being movable between index positions in response to movement of the patient's arm, said cuff support member transmitting the force of movement of the patient's arm from said cuff to said index member to move said index member between index positions;

wherein said cuff support member is an elongate member extending between said index member and said cuff, said apparatus further comprising a free guide for guiding and stabilizing said cuff support member at a location along the length of said support member intermediate said index member and said cuff member, said free guide including:

a guide member engaging said support member at a position off the table, and guide member support means connected with said guide member for supporting said guide member on the table and for enabling movement and positioning of said guide member in a first direction along the length of the table, in a second direction across the width of the table, and in a third direction generally normal to the upper major side surface of the table.

5. An apparatus as set forth in claim 4 wherein said cuff member has surfaces defining a thumb opening for receiving therethrough the patient's thumb and a wrist bone opening for receiving therethrough the patient's wrist bone.

6. Apparatus for controlling movement of a joint of a patient's body during imaging of the joint within the bore of an MRI unit having a primary coil, said apparatus comprising:

a support block fixable in position relative to the primary coil;

an index disk confined for rotation about an axis and in a single plane within a recess in said support block, said index disk having first and second major side surfaces which face in axially opposite directions and an intermediate portion extending therebetween;

rotation control means connected in force-transmitting relationship between said support block and said index disk for contacting said index disk to block rotation of said index disk within the recess in said block;

a cuff for connection with a portion of the patient's body which is adjacent the joint being imaged; and a rigid cuff support interconnecting said index disk and said cuff and fixing said cuff for rotation with said index disk between a plurality of successive imaging positions corresponding to positions of rotation of said index disk.

7. Apparatus as set forth in claim 6 wherein said rotation control means is movable between a first condition blocking rotational movement of said index disk and a second position allowing rotational movement of said index disk relative to said support block.

8. Apparatus as set forth in claim 7 wherein said rotation control means includes means for retaining said index disk in a selected one of a series of predetermined repeatable positions of rotation relative to said support block and for blocking movement of said index disk out of a selected position of rotation.

9. Apparatus as set forth in claim 8 comprising a handle connected in force-transmitting relationship with said index disk, said handle being manually engageable and movable by an operator other than the patient being imaged to effect rotation of said index disk between successive positions of rotation and of said cuff between successive imaging positions.

10. Apparatus as set forth in claim 8 wherein said means for retaining said index disk in a selected one of a series of predetermined repeatable positions and for blocking movement of said index disk out of the selected position of rotation includes surfaces defining a plurality of index openings disposed in a circular pattern on said index disk, said index openings moving along a circular path as said index disk rotates, and a plunger mounted for sliding movement toward and away from said index disk openings.

11. Apparatus as set forth in claim 10 wherein said means for retaining said index disk in the selected one of a series of predetermined repeatable positions and for blocking movement of said index disk out of the selected position of rotation includes a trigger mechanism connected with said plunger and having a first condition blocking movement of the plunger toward said index disk openings when the plunger is retracted away from said index disk and a second condition freeing the plunger for movement toward said index disk openings, said trigger mechanism being moved from the first condition to the second condition as a result of rotation of said index disk by force transmitted from the patient through said cuff member and said support member.

12. Apparatus as set forth in claim 6 wherein said rotation control means includes surfaces defining a plurality of index openings disposed in a circular pattern on said index disk, the index openings revolving along a circular path as said index disk rotates, and a plunger mounted for sliding movement relative to the index disk openings between a first position in engagement with one of the openings and blocking movement of said index disk out of a selected position of rotation and a second position not in engagement with any one of the openings and allowing rotational movement of said index disk relative to said support block.

13. A shoulder indexing apparatus for use during magnetic resonance imaging of a shoulder joint of a patient, with the patient lying on a generally planar imaging table having a foot end and a head end and being slidable into and out of a primary imaging coil of a magnetic resonance imaging unit, said shoulder indexing apparatus comprising:

an indexer base for attachment to the foot end of the table;

an indexer body supported on said indexer base;

an index disk rotatably received in said indexer body and rotatable relative to said indexer body about an axis extending generally parallel to the length of the imaging table;

a clamp block fixed to said index disk for rotation with said index disk;

an elongate cuff support member extending axially along the table for a substantial distance from the foot end toward the head end of the table through aligned openings in said clamp block and said index disk;

a cuff for clamping onto the patient's arm when the patient is lying on the table with the patient's feet at the foot end of the table and the patient's head at the head end of the table, said cuff being supported on said cuff support member at an end of said cuff support member remote from said index disk for rotational movement with said support member and with said index disk about said axis;

a lock member releasably interconnecting said support member and said clamp block;

index locking means connected between said indexer base and said index disk and movable between a first condition blocking rotation of said index disk relative to said indexer base and a second condition enabling rotation of said index disk relative to said indexer base; and a trigger mechanism connected with said index locking means and operable in response to rotation of said index disk by force transmitted from the patient through said cuff member and said support member to move said index locking means between the first condition blocking rotation of said index disk relative to said indexer base and a second condition enabling rotation of said index disk relative to said indexer base.

14. An apparatus as set forth in claim 13 comprising means for securing said indexer base to the table in any selected one of a plurality of positions spaced apart laterally in a direction transverse to the axis.

15. An apparatus as set forth in claim 13 comprising an actuator engageable by the patient at a location remote from said indexing mechanism, said actuator being connected with said index mechanism for allowing movement of said indexing mechanism, upon actuation by the patient, into the next sequential index position, said actuator comprising an elongate flexible member connected with said index locking means for transmitting actuating force from the patient's hand to said index locking means to move said index locking means into the second condition.

* * * * *